(12) United States Patent
Muzykantov et al.

(10) Patent No.: US 7,172,760 B2
(45) Date of Patent: Feb. 6, 2007

(54) COMPOSITIONS AND METHODS FOR PREVENTION AND TREATMENT OF UNCONTROLLED FORMATION OF INTRAVASCULAR FIBRIN CLOTS

(75) Inventors: Vladimir R. Muzykantov, Warwick, PA (US); Abd Al-Roof Higazi, Bala Cynwyd, PA (US); Juan Carlos Murciano, Sevilla (ES); Douglas Cines, Wynnewood, PA (US); Ronald P. Taylor, Charlottesville, VA (US)

(73) Assignees: Trustees of the University of Pennsylvania, Philadelphia, PA (US); University of Virginia Patent Foundation, Charlottesville, VA (US)

( * ) Notice: Subject to any disclaimer, the term of this patent is extended or adjusted under 35 U.S.C. 154(b) by 201 days.

(21) Appl. No.: 10/253,518

(22) Filed: Sep. 23, 2002

(65) Prior Publication Data
US 2003/0152563 A1    Aug. 14, 2003

Related U.S. Application Data

(60) Division of application No. 09/454,666, filed on Dec. 3, 1999, now Pat. No. 6,488,927, which is a continuation-in-part of application No. PCT/US99/10547, filed on May 12, 1999.

(60) Provisional application No. 60/086,262, filed on May 21, 1998.

(51) Int. Cl.
*A61K 39/00* (2006.01)
*A61K 38/49* (2006.01)
*C12N 9/72* (2006.01)
*C12N 9/70* (2006.01)
*C12N 9/96* (2006.01)

(52) U.S. Cl. ............... 424/178.1; 424/94.3; 530/378.1; 435/188

(58) Field of Classification Search ............ 514/2, 514/25; 424/178.1, 94.3; 530/350, 378.1; 435/188
See application file for complete search history.

(56) References Cited

FOREIGN PATENT DOCUMENTS
EP            485749       *  5/1992

OTHER PUBLICATIONS

Database Caplus DN 104:47840 Kamimura et al JP 60200169 Oct. 9, 1985.*

Lutz et al Biochim Biophys Acta. Mar. 5, 1992;1116(1):1-10; see abstract.*

Birmingham et al. J Lab Clin Med. Aug. 1990;116(2):242-52; see abstract.*

Collen, D., "Fibrin-Selective Thrombolytic Therapy for Acute Myocardial Infarction", 1996 *Circulation* 93:857-865.

Heeremans, J. et al., "The Preparation of Tissue-Type Plasminogen Activator (t-PA) Containing Liposomes:Entrapment Efficiency and Ultracentrifugation Damage", 1995 *J. Drug Targeting* 3:301-310.

Higazi, A. et al., "Enhancement of the Enzymatic Activity of Single-chain urokinase Plasminogen Acitivator by Soluble Urokinase Receptor", 1995 *J. Biol. Chem.* 270:17375-17380.

Higazi, A. et al., "Single-Chain Urokinase-Type Plasminogen Activator Bound To Its Receptor Is Relatively Resistant To Plasminogen Activator Inhibitor Type 1", 1996 *Blood* 87:3545-3549.

Kajihara, J. et al., "Physicochemical characterization of PEG-PPG conjugated human urokinase", 1994 *Biochim. Biophys. Acta* 1199:202-208.

Muzykantov, V. et al., "Avidin Attachment to Biotinylated Erthrocytes Induces Homologous Lysis Via the Alternative Pathway of Complement", 1991 *Blood* 78:2611-2618.

Muzykantov, V. and R. Taylor, "Attachment of Biotinylated Antibody to Red blood Cells: Antigen-Binding Capacity of Immunoerythrocytes and Their Susceptibility to Lysis by Complement", 1994 *Anal. Biochem.* 223:142-148.

Muzykantov, V. et al., "Regulation of the Complement-Mediated Elimination of Red Blood Cells Modified with Biotin and Strepatavidin", 1996 *Anal. Biochem.* 241:109-119.

Muzykantov, V. et al., "The Functional Effects of Biotinylation of Anti-angiotensin-Converting Enzyme Monoclonal Antibody in Terms of Targeting *in Vivo*", 1995 *Anal. Biochem.*, 226:279-287.

Muzykanotv, V. et al., "Targeting of Antibody-Conjugated Plasminogen Activators to the Pulmonary Vasculature", 1996 *J. Pharm. Exp. Ther.*, 279:1026-1034.

Runge, M. et al., "Enhanced Thrombolytic and Antithrombotic Potency of a Fibrin-Targeted Plasminogen Activator in Baboons", 1996 *Circulation* 94:1412-1422.

Suzuki, T. and G. Dale, "Biotinylated Erythrocytes: In Vivo Survival and In Vitro Recovery", 1987 *Blood* 70:791-795.

Zaltman, A. et al., "Enhanced complement susceptibility of avidin-biotin-treated human erythrocytes is a consequence of neutralization of the complement regulators CD59 and decay accelerating factor", 1995 *Biochem. J.* 307:651-656.

* cited by examiner

*Primary Examiner*—Michael Borin
(74) *Attorney, Agent, or Firm*—Licata & Tyrrell P.C.

(57) ABSTRACT

Compositions and methods for prevention and treatment of uncontrolled formation of intravascular fibrin clots are provided wherein fibrinolytic or anticoagulant drugs are biocompatibly coupled to red blood cell carriers.

3 Claims, No Drawings

COMPOSITIONS AND METHODS FOR PREVENTION AND TREATMENT OF UNCONTROLLED FORMATION OF INTRAVASCULAR FIBRIN CLOTS

INTRODUCTION

This application is a divisional of U.S. patent application Ser. No. 09/454,666, filed Dec. 3, 1999, now U.S. Pat. No. 6,488,927, which is a continuation-in-part of PCT Application PCT/US99/10547 filed May 12, 1999, which claims the benefit of priority from U.S. Provisional Application Ser. No. 60/086,262 filed May 21, 1998.

BACKGROUND OF THE INVENTION

Occlusions of blood vessels by intravascular clots cause or/and contribute to the pathogenesis of a variety of disease conditions including myocardial infarction, stroke and pulmonary embolism and thus represent a significant medical problem. Although fibrinolytics, such as plasminogen activators, have recently been used in the treatment of some of these diseases or conditions, their effectiveness and safety are still of a great concern, especially under specific prothrombotic conditions such as deep vein thrombosis and pulmonary embolism.

Pulmonary thromboembolism, a leading cause of mortality, is most often a complication of deep venous thrombosis. Statistics show that more than 95% of pulmonary emboli result from thrombi in the deep venous system of the lower extremities. Despite advances in medicine, the incidence and/or recognition of embolism and deep vein thrombosis appears to be increasing. This increase has been attributed to higher survival of trauma patients, an increase in orthopedic surgeries for joint replacement, and the widespread use of indwelling catheters, as well as the overall increase in medical and surgical procedures, particularly in older patients. As a result, methods of preventing and treating deep vein thrombosis are required to reduce the incidence of pulmonary embolisms.

Factors which promote deep vein thrombosis were defined as early as the nineteenth century and include stasis, abnormalities of the blood vessel wall, and alterations in the blood coagulation system. The highest risk groups for deep vein thrombosis are surgical patients requiring 30 minutes or more of general anesthesia, postpartum patients, patients with right and left ventricular failure, patients with fractures or injuries involving the lower extremities, patients with chronic deep venous insufficiency of the legs, patients on prolonged bed rest, cancer patients, obese individuals, and patients using estrogens. Treatment of deep vein thrombosis most often involves use of an anticoagulant such as heparin. Even with this well-known drug, however, there is no consensus regarding the optimum regimen of anticoagulant therapy that affords both safety and efficacy. In addition to anticoagulant therapy, thrombolytic agents, such as streptokinase and urokinase, have been used in the management of acute deep vein thrombosis.

Streptokinase, staphylokinase, tissue-type plasminogen activator or tPA, and urokinase are members of a family of agents known as plasminogen activators. These compounds act to dissolve intravascular clots by activating plasmin, a protease that digests fibrin. Plasminogen, the inactive precursor of plasmin, is converted to plasmin by cleavage of a single peptide bond. Plasmin itself is a nonspecific protease that digests fibrin clots as well as other plasma proteins, including several coagulation factors.

Fibrinolytic therapy with plasminogen activators have been shown to be useful in the treatment of myocardial infarction and stroke. However, application of these agents to dissolution of clots formed or lodged in other vascular areas such as deep venous areas is limited by extremely rapid elimination and inactivation after bolus dosing (Plow, E. et al. 1995. *FASEB J.* 9:939–945; Narita, M. et al. 1995. *J. Clin. Invest.* 96:1164–1168). Both tPA and urokinase undergo rapid inactivation by a circulating plasminogen activator inhibitor and plasmin itself is inactivated by a circulating glycoprotein, α-2-antiplasmin (Collen, D. 1996. *Circulation* 93:857–865; Reilly, C. et al. 1991. *Arterioscl. Thromb.* 11:1276–1286). α-2-antiplasmin inactivates staphylokinase, while streptokinase is more resistant to this endogenous glycoprotein inhibitor (Collen, B. et al. 1993. *Eur. J. Biochem.* 216:307–314). Although therapeutic doses of plasminogen activators can overwhelm the potential inhibitory activity of plasminogen activator inhibitor and α-2-antiplasmin, other inhibitors of plasminogen activators also are present (C1-inhibitor, α-2-macroglobulin, antitrypsin) and contribute to the decrease over time in the fibrinolytic response upon treatment with plasminogen activators (Collen, D. 1996. *Circulation* 93:857–865). Such inactivation, or degradation of plasminogen activators and plasmin reduce the effectiveness of thrombolytic therapy and thus fail to prevent re-occlusion of blood vessels.

To overcome this problem, attempts have been made to infuse plasminogen activators intravenously for prolonged periods of time with little success; failure was attributed to the harmful side effects such as bleeding and uncontrolled tissue proteolysis that occurred, likely after extra vascular deposition of plasminogen activators.

Accordingly, several different approaches have been attempted to improve efficacy of these agents in deep vein thrombosis including: prolongation of the half-life of plasminogen activators in blood; protection of plasminogen activators from inactivation by inhibitors; and targeting plasminogen activators to fibrin and thrombi. For example, chemical modifications and incorporation of plasminogen activators into liposomes have been used to prolong the half-life of plasminogen activators in the circulation (Kajihara, J. et al. 1994. *Biochim. Biophys. Acta* 1199:202–208; Heeremans, J. et al. 1995. *Thromb. Haemost.* 73:488–494). However, these studies have shown that the activity of liposome-encapsulated plasminogen activators is strongly compromised by steric limitations. Genetically engineered tPA compounds have also been produced which possess altered pharmacokinetic properties, enhanced resistance to inhibitors, and higher fibrinolytic potency (Collen, D. 1996. *Circulation* 93:857–865; Collen, D. 1993. *Lancet* 342:34–36; Krishnamurti, C. et al. 1996. *Blood* 87:14–19; Lijnen, R. and D. Collen. 1992. *Ann. NY Acad. Sci.* 667: 357–364). Several laboratories have explored conjugation of plasminogen activators with antibodies recognizing fibrin or activated platelets in order to localize plasmin generation to the clot (Holvoet, P. et al. 1993. *Circulation* 87:1007–1016; Runge, M. et al. 1996. *Circulation* 94:1412–1422; Fears, R. and G. Poste. 1994. *Fibrinolysis* 8:203–213). However, such conjugated plasminogen activators with affinity for clot components only bind to the superficial layer of the clot and do not enter into the clot interior (Sakharov, D. and D. Rijken. 1995. *Circulation* 92:1883–1890). In addition, clots bind only a small fraction of injected "fibrin-specific" plasminogen activator because of limited surface area of the formed clots.

Further, to date, none of these methods for modifying plasminogen activators prevents deposition of plasminogen activators in tissues, which can lead to an increase in harmful side effects; they all represent molecules or molecular complexes with sizes that do not exceed that of blood proteins. Such deposition leads to plasmin activation in tissues. Activated plasmin degrades the extracellular matrix, thus causing vascular remodeling, abnormal elevation of vascular permeability and even partial denudation of subendothelium (Plow et al. 1995. *FASEB J.* 9:939–945; Shreiber et al. 1995. *J. Cell. Physiol.* 165:107–118).

Accordingly, there is a need for methods of modifying plasminogen activators which not only decrease the rate of elimination and degradation of the plasminogen activators, but also prevent deposition of the plasminogen activator in the tissues.

Red blood cells (RBCs) normally have a life span of 120 days and thus can serve as natural carriers for drugs and biomolecules. Autologous RBCs can be easily obtained from the patient's blood, loaded with drug, and re-injected. RBCs have been used as carriers for drugs loaded into the inner volume of RBCs (Poznansky, M. and R. Juliano. 1984. *Pharmacol. Rev.* 36:277–324; Kirch, M. et al. 1994. *Biotechnol. App. Biochem.* 19:331–363; Kinoshita, K. and T. Tsong. 1978. *Nature* 272:258–260). In addition, methods for conjugation of proteins to RBCs have been developed, including methods using a streptavidin-biotin pair as a cross-linker.

Streptavidin is a 60 kDa protein that possesses four high affinity biotin binding sites and the streptavidin-biotin pair is widely used in biomedicine as a cross-linking agent (Wilchek, M. and E. Bayer. 1988. *Anal. Biochem.* 171: 1–32). Several groups have reported application of streptavidin-biotin technology in vivo for gamma-immunoscintigraphy (Kalofonos, H. et al. 1990. *J. Nucl. Med.* 31:1791–1796) and drug targeting (Pardridge, W. et al. 1995. *Proc. Natl. Acad. Sci. USA* 92:5592–5596; Muzykantov, V. et al. 1996. *Proc. Natl. Acad. Sci. USA* 93:5213–5218). Moreover, streptavidin induces no known harmful reactions in animals or humans (Kalofonos, H. et al. 1990. *J. Nucl. Med.* 31:1791–1796). Biotinylation of RBCs can be accomplished in manner which has no effect on the life span and biocompatibility of these cells in vivo in animals (Susuki, T. and G. Dale. 1987. *Blood* 70:791–795; Muzykantov, V. et al. 1991. *Blood* 78:2611–2618).

Biotinylation of proteins, including plasminogen activators, without significant reduction of functional activity of the plasminogen activator has been described (Muzykantov, V. et al. 1986. *Biochem. Biophys. Acta*, 884:355–363; Muzykantov, V. et al. 1995. *Anal. Biochem.*, 226:279–287; Muzykantov, V. et al. 1996. *J. Pharm. Exp. Ther.*, 279:1026–1034). In in vitro studies, polyvalent conjugation of various biotinylated proteins such as antibodies, enzyme peroxidase and fibrinolytic streptokinase with streptavidin conjugated-biotinylated RBCs (SA/b-RBC) was performed and high functional activity of these proteins bound to SA/b-RBC in vitro was reported (Muzykantov, V. et al. 1985. *FEBS Lett.* 182:62–66; Muzykantov, V. et al. 1986. *Biochim. Biophys. Acta* 884:355–363; Muzykantov, V. et al. 1987. *Am. J. Pathol.* 128:226–234).

However, polyvalent conjugation of biotinylated proteins to b-RBCs via streptavidin cross-linker profoundly compromises the biocompatibility of the carrier RBC. Binding of streptavidin to b-RBC leads to elimination of homologous restriction of both classical and alternative pathways of the complement thereby causing lysis of SA/b-RBC in the plasma (Muzykantov, V. et al. 1991. *Blood* 78:2611–2618; Muzykantov, V. et al. 1992. *Int. J. Artif. Organs* 15:620–627; Muzykantov, V. et al. 1993. *FEBS Lett.* 318:108–112). Streptavidin-induced cross-linking and membrane redistribution of the complement inhibitors, DAF and CD59, in biotinylated RBC membrane represents the likely mechanism for complement activation and lysis (Muzykantov, V. et al. 1992. *Biochim. Biophys. Acta* 1107:119–125; Zaltzman, A. et al. 1995. *Biochem. J.* 305:651–656). In addition, fixation of C3b complement component has been shown to lead to an increased rate of elimination of SA/b-RBC from the bloodstream via hepatic and splenic uptake (Muzykantov, V. et al. 1992. *Int. J. Artif. Organs* 15:620–627; Muzykantov, V. et al. 1996. *Anal. Biochem.* 214:109–119). Accordingly, drugs polyvalently conjugated to an RBC carrier via streptavidin can not be delivered to their targets in vivo.

This lack of biocompatibility of SA/b-RBC carrier can be overcome through modifications of the conjugation method. For example, monovalent coupling of streptavidin to b-RBCs has been demonstrated to produce a serum-stable carrier SA/b-RBC capable of binding up to $10^5$ molecules of a biotinylated model protein per RBC (Muzykantov, V. et al. 1991. *Biochem. J.* 273:393–397; Muzykantov, V. et al. 1992. *Biochim. Biophys. Acta* 1107:119–125; Muzykantov, V. et al. 1993. *Anal. Biochem.* 208:338–342; Muzykantov, V. and R. Taylor. 1994. *Anal. Biochem.* 223:142–148; Muzykantov, V. et al. 1996. *Anal. Biochem.* 214:109–119;). B-RBC carrier, monovalently conjugated with a model biotinylated protein (b-IgG) via streptavidin, circulated for at least a day as a stable complex after intravenous injection in animals, with no evidence of lysis or hepatic uptake (Muzykantov, V. et al. 1996. *Anal. Biochem.* 214:109–119). In these studies, it was also found that the half-life b-IgG monovalently conjugated with SA/b-RBCs significantly exceeded that of non-conjugated b-IgG (Muzykantov, V. et al. 1996. *Anal. Biochem.* 214:109–119).

It has now been found that monovalent conjugation of a biotinylated plasminogen activator to a SA/b-RBC carrier results in prolonged circulation of the plasminogen activator in the bloodstream and decreased deposition of the plasminogen activator in the tissues. It has also now been found that monovalent conjugation of biotinylated soluble receptor for urokinase plasminogen activator, (b-suPAr), and monovalent conjugation of biotinylated tissue plasminogen activator, (tPA), to a SA/b-RBC carrier results in prolonged circulation of these biotinylated plasminogen activators in the bloodstream in a form of the receptor/RBC complex (b-suPAr/SA/b-RBC complex) and the tPA/RBC complex, respectively. Moreover, it has now been found that the b-suPAr/SA/b-RBC complex retains its ability to bind single chain urokinase plasminogen activator (scuPA) even after prolonged circulation in the bloodstream and that non-covalent binding of this fibrinolytic precursor (scuPA) to the receptor conjugated to RBC carrier (i.e., to b-suPAr/SA/b-RBC complex) leads to scuPA activation and greater resistance to plasma inhibitors and thus provides increased fibrinolytic activity on the clot itself. It has also been found that pulmonary vascular uptake of tPA is increased by crosslinking tPA to biotinylated RBC to form a tPA/RBC complex, with the increase seen to a level that exceeds the level of tPA/RBC complex in larger blood vessels. Finally, it has now been found that conjugation of tPA and suPAr with a monoclonal antibody against human CR1 promotes specific coupling of fibrinolytically active anti-thrombotic agents to red blood cells, limiting the non-specific binding and tissue uptake of the complexes. Accordingly, the present invention relates to compositions comprising a fibrinolytic or anticoagulant drug biocompatibly coupled to a carrier red blood cell molecule and methods of using these compositions in the treatment of uncontrolled intravascular clot formation including deep vein thrombosis.

SUMMARY OF THE INVENTION

An object of the present invention is to provide compositions which comprise a fibrinolytic or anticoagulant drug biocompatibly coupled to the surface of red blood cell carrier. In one embodiment, this coupling is accomplished by crosslinking biotinylated tissue plasminogen activator to biotinylated red blood cells via streptavidin. In another embodiment, biotinylated tissue plasminogen activator is crosslinked via streptavidin to biotinylated molecules such as monoclonal antibodies which then couple specifically with red blood cells as carriers. An example of a monoclonal antibody specific for red blood cells is a monoclonal antibody against human CR1.

Another object of the present invention is to provide a method for decreasing the rate of elimination of a fibrinolytic or anticoagulant drug from blood and decreasing deposition of the drug in tissues by biocompatibly coupling the drug to red blood cell carriers.

Another object of the present invention is to provide a method for activating a precursor of fibrinolytic, single chain urokinase plasminogen activator (scuPA) in blood which comprises binding of scuPA to its receptor which is biocompatibly coupled to red blood cell carriers.

Another object of the present invention is to provide a method for increasing pulmonary vascular uptake of tissue plasminogen activator which comprises coupling tissue plasminogen activator to red blood cells and administering the tissue plasminogen activator coupled to the red blood cell to an animal.

Another object of the present invention is to provide a method for increasing degradation of existing intravascular fibrin clots by a fibrinolytic drug in blood of a patient which comprises administering to a patient a composition comprising a fibrinolytic drug biocompatibly coupled to red blood cell carriers.

Yet another object of the present invention is to provide a method of preventing and treating uncontrolled formation of intravascular clots in a patient which comprises administering to a patient suffering from uncontrolled formation of intravascular clots a composition comprising a fibrinolytic or anticoagulant drug biocompatibly coupled to red blood cell carriers.

DETAILED DESCRIPTION OF THE INVENTION

The present invention provides compositions and methods for prevention and treatment of deep vein thrombosis, pulmonary embolism and other diseases or syndromes characterized by uncontrolled formation of intravascular fibrin clots. The invention is based on the biocompatible coupling of a drug, preferably a fibrinolytic or anticoagulant drug, more preferably a plasminogen activator, to RBCs which serve as carriers providing prolonged circulation and restricted tissue uptake of the drug. The monovalent conjugation of plasminogen activators to biotinylated RBCs via streptavidin (referred to herein as SA/b-RBC) serves as an example in the present invention of a biocompatible coupling method. Biotinylated plasminogen activators are referred to herein as b-PAs. Another example of biocompatible coupling is the crosslinking of plasminogen activators to biotinylated molecules such as monoclonal antibodies which then couple specifically with red blood cells in whole blood. An example of an antibody useful in this coupling method is a monoclonal antibody against human CR1.

Experiments were performed to examine the conjugation of b-PAs to biotinylated RBCs via streptavidin. Results of in vitro tests showed that streptavidin provided specific and effective conjugation of the b-PAs to the biotinylated RBC (Table 1).

TABLE 1

Number of $^{125}$I-coupled Plasminogen Activator Molecules Per Red Blood Cell

| Plasminogen Activator | # Coupled to Biotinylated RBCs | # Coupled to SA/ biotinylated RBCs |
|---|---|---|
| biotinylated-scuPa | <400 | 79,000 |
| biotinylated-tPA | <400 | 30,000 |
| biotinylated-urokinase | <1200 | 42,000 |
| biotinylated-streptokinase | <300 | 12,000 |

When tested in a fibrin plate lysis assay and in an assay of release of radio labeled iodine from a fibrin clot (formed from $^{125}$I-fibrinogen), the b-PA/SA/b-RBC conjugates were shown to be stable and to display high fibrinolytic activity. When the b-PA/SA/b-RBC conjugates were added to solution of $^{125}$I-fibrinogen before formation of fibrin clot, the subsequent fibrinolysis attained 71±12%. Non-conjugated PAs induced 96±5.5% lysis of fibrin clot. Thus, conjugation of b-PA to SA/b-RBC does not compromise significantly fibrinolytic activity of PA.

The half-life (i.e., rate of degradation and elimination from blood) of RBC-conjugated plasminogen activators was also examined in vivo in rats. The kinetics of blood clearance of $^{125}$I-scuPA, $^{125}$I-urokinase, $^{125}$I-streptokinase, or $^{125}$I-tPA were determined following intravenous injection of scuPA or tPA at a dose of 5 µg/kg. Within one hour of injection, the blood level of scuPA dropped to less than 5% of the injected dose. In contrast, the blood level of SA/b-RBC-conjugated scuPA was 10-fold higher at the one hour time point, and remained at high levels (20% of injected dose) for up to 24 hours. Similar results were seen with tPA, urokinase and streptokinase. Pharmacokinetic analysis of the areas below the curves of blood level of plasminogen activators versus those biocompatibly coupled to RBC during 24 hours after intravenous injection revealed that the half-life of RBC-conjugated PAs exceeded that of non-conjugated PAs by several orders of magnitude.

Further, conjugation of the biotinylated plasminogen activators with SA/b-RBC carrier did not cause intravascular lysis of the carrier RBC labeled with $^{51}$Cr and did not change the biodistribution of RBC in any tissues except the spleen. Splenic uptake of the b-PA/SA/b-RBC was elevated about 4-fold. However, such increases in splenic uptake of chemically modified RBCs are well known in the literature. Importantly, after injection of b-PA/SA/b-RBC conjugates, tissue uptake of plasminogen activators was markedly reduced. For example, level of $^{125}$I-tPA in the brain tissue (expressed as percentage of that in the blood) was 18.3±1.1%, whereas that parameter for $^{125}$I-b-tPA/SA/b-RBC was 1.8±0.5%. Thus conjugation with RBC carrier provides ten fold reduction of the uptake in the brain.

In the case of tPA, the tissue distribution data revealed that conjugation of tPA to RBC not only prolonged its bioavailability in the circulation, but also dramatically increased its pulmonary vascular uptake. One hour after injection, 20% of the radiolabeled tPA was found in the lungs of rats injected with $^{125}$I-tPA/RBC, a value that is 100-fold higher than what is seen following injection of soluble $^{125}$I-tPA. Yet, the pulmonary uptake of tPA/$^{51}$Cr-RBC was only marginally higher than that of non-modified RBC (3.8% versus 1.2%). Thus, the lungs of rats injected with tPA/RBC contained five-fold more radiolabeled tPA than radiolabeled RBC, whereas the ratio of radiolabeled tPA to radiolabeled RBC equaled one in all other tissues, including blood. This indicates that there was a significant transfer of tPA to the lung, the pulmonary vasculature, a result that was not seen in other organs (an organ-specific effect). This transfer of tPA from the carrier RBC occurred rapidly and lasted for several hours. In addition, the lung to blood ratio of 125I-tPA/RBC was 20 times higher than that of radiolabeled tPA whereas in the kidney, brain and heart, these organ to blood ratios were ten times lower, data indicating that coupling of tPA to RBC strongly restricted uptake by organs other than the lung.

Experiments were also performed to determine strategies for activating inactive plasminogen activators in blood. The soluble form of urokinase receptor (suPAr) has been reported to bind scuPA and convert inactive scuPA to an active uPA, as well as protect it from inhibition by plasma inhibitors (Higazi, A. et al. 1995. *J. Biol. Chem.* 270: 17375–17380; Higazi, A. et al. 1996. *Blood* 87:3545–3549). The half-life of suPAr in blood, however, is short, in the range of minutes following intravenous injection. Accordingly biotinylated suPAr was coupled to SA/biotinylated RBCs to prolong the half-life of suPAr in vivo. This coupling yielded a complex designated as b-suPAr/SA/b-RBC that possessed up to $1.3 \times 10^5$ molecules of suPAr per SA/b-RBC molecule. Without streptavidin conjugated to the biotinylated RBCs, the binding of suPAr to the RBC carrier was an order of magnitude lower ($1.2 \times 10^4$ suPAr molecules/RBC).

The ability of b-suPAr/SA/b-RBC complex to bind single chain urokinase plasminogen activator (scuPA) was examined in vitro by incubating $^{125}$I-labeled scuPA with b-suPAr/SA/b-RBC or intact RBCs (used as a control of non-specific binding of scuPA). It was found that $1.5 \pm 0.1 \times 10^4$ molecules of $^{125}$I-scuPA per b-suPAr/SA/b-RBC bound while only $0.06 \pm 0.01 \times 10^4$ $^{125}$I-scuPA per RBC bound. Thus, the b-suPAr/SA/b-RBC complex binds scuPA effectively and specifically.

The fibrinolytic activity of the scuPA associated with b-suPAr/SA/b-RBC complex (scuPA/b-suPAr/SA/b-RBC) was then examined. Fibrin clots were prepared that contained $^{125}$I-fibrin and either phosphate-buffered saline (control clots), RBC carrier alone, b-scuPA/SA/b-RBC complexes, scuPA/b-suPAr/SA/b-RBC complexes, or scuPA alone. In control clots, less than 5% of the radiolabel was released to the supernatant after 120 minutes incubation at 37° C. Neither RBC carrier alone nor b-scuPA/SA/b-RBC complexes (b-scuPA conjugated to SA/b-RBC directly) caused detectable fibrinolysis. Free scuPA caused about 10% fibrinolysis. However, similar doses of scuPA/b-suPAr/SA/b-RBC complexes caused 95±4% fibrinolysis. These results indicate that binding of scuPA to b-suPAr conjugated with SA/b-RBC indeed stimulates fibrinolytic activity of scuPA and that b-suPAr/SA/b-RBC complex is active as a fibrinolytic agent.

To determine the fate of the b-suPAr/SA/b-RBC complex in vivo, rats were injected intravenously with $^{125}$I-suPAr/SA/$^{51}$Cr-b-RBC and the blood levels and biodistribution of the complex were studied. Conjugation of suPAr to the carrier RBC significantly increased the half-life of suPAr in the bloodstream. The blood level of non-conjugated suPAr was undetectable within 3 hours, while 20% of the b-suPAr/SA/b-RBC complex was measurable out to 24 hours after injection.

Biodistribution studies showed that conjugation of suPAr did not lead to hemolysis or to reticuloendothelial uptake of the carrier RBC. In fact, distribution of the conjugated b-suPAr/SA/$^{51}$Cr-b-RBC was similar to that of the control $^{51}$Cr-RBC distribution. One hour after injection of rats with b-suPAr/SA/$^{51}$Cr-b-RBC, blood samples were obtained for determination of binding of $^{125}$I-scuPA to blood cells. Blood obtained from rats injected with the b-suPAr/SA/b-RBC complexes bound three times more scuPA than blood obtained from control animals. These data indicate that b-suPAr/SA/b-RBC is functionally active in the circulation and is capable of binding scuPA. Quantitation of the binding revealed that, after circulating for one hour in the bloodstream, each b-suPAr/SA/b-RBC complex binds approximately $10^4$ molecules of scuPA. This value is similar to the initial levels of scuPA binding of b-suPAr/SA/RBC before injection in rats. Therefore, circulation in the bloodstream did not alter the binding ability of this complex.

The fibrinolytic activity of crosslinked plasminogen activators was examined in vivo in rats. Rats were injected intravenously with either 250 μg of unconjugated tPA or 50 μg of tPA conjugated to carrier RBC and blood was collected after 10, 60 and 180 minutes. $^{125}$I-fibrinogen was added to all samples and blood was allowed to coagulate at room temperature. Neither tPA nor tPA/RBC suppressed clot formation at the test concentrations, an important consideration in terms of safety of the present invention. The clots were then incubated at 37° C. and the rate of clot lysis was examined. Spontaneous fibrinolysis did not exceed 10% at either 10 minutes or 60 minutes in rats injected with saline. Fibrinolysis was augmented 10 minutes after injection of unconjugated tPA. However, the rate of fibrinolysis in blood obtained 60 minutes after tPA injection only marginally exceeded that of the control animals, as was expected in light of the rapid elimination of tPA from blood. Remarkably, blood obtained even 3 hours after tPA/RBC injection retained significant fibrinolytic activity (40% clot lysis), even though the injected dose of tPA was 5-fold lower. These data show that conjugation of tPA to the carrier RBC significantly increased the circulation of enzymatically active plasminogen activator in vivo and prolonged the in vivo half-life of the plasminogen activator in blood to a level that would overcome any steric limitations that might be imposed by conjugation to RBC.

Experiments were also performed with mouse RBCs. In these experiments, tPA was conjugated to washed murine RBC in Krebs-Ringer buffer containing glucose and 3% bovine serum albumin to minimize energy depletion and mechanical damage. Using methods as described for rat RBCs, 3 to $4 \times 10^4$ molecules of biotinylated tPA or suPAr per biotinylated murine RBC were coupled without detectable hemolysis as shown below in Table 2. In these tests, the murine RBC were biotinylated with 10 μM BxNHS in Krebs-Ringer glucose (pH 7.4). The radiolabeled activators were coupled to b-RBC via streptavidin in BSA-containing Krebs-Ringer glucose. Therefore, murine RBC were conjugated in the same way as human and rat RBCs.

TABLE 2

Coupling Efficiency of Murine RBC

| Activator | Added (per RBC) | Bound (per RBC) | % Added (of RBC) | Bound (per SA/b-RBC) | % Added (of SA/b RBC) |
|---|---|---|---|---|---|
| $^{125}$I-b-tPA | $3 \times 10^5$ | $4.4 \times 10^3$ | 1.5% | $3.2 \times 10^4$ | 11% |
| $^{125}$I-b-suPAr | $2 \times 10^5$ | $3.5 \times 10^2$ | 0.2% | $4.1 \times 10^4$ | 20% |

Experiments were also performed to determine whether conjugation of soluble uPA receptor (suPAr) to RBCs prolongs its half-life in mice as was observed in rats. Radiolabeled suPAr or RBC/suPAr complexes were generated with b-RBC and then injected intravenously in mice. Conjugation of suPAr did not accelerate splenic or hepatic uptake of the carrier murine RBC. Moreover, coupling to the carrier murine RBC prolonged the circulation of suPAr by several orders of magnitude from several minutes to several hours.

Experiments were also performed with monoclonal antibodies as the RBC carrier molecules. In these experiments, the human monoclonal antibody CR1 was used. b-tPA and b-suPAr were conjugated to biotinylated monoclonal antibody 1B4 directed against human CR1 using a streptavidin crosslinker. Using methods similar to those with the ex vivo carrier, the anti-CR1/$^{125}$I-tPA and anti-CR1/$^{125}$I-suPAr heteropolymers were shown to bind specifically to naive human RBC in whole blood (Table 3). The amount of tPA and suPAr coupled ($2–3 \times 10^3$ molecules per RBC) was equivalent to what was produced for other anti-CR1 conjugated proteins (Muzykantov and Taylor 1994. *Anal. Biochem.* 223:142–148). The conjugation of b-tPA via the antibody suppressed the non-specific adhesiveness by an order of magnitude (<100 molecules of IgG/$^{125}$I-tPA bound per naive RBC versus 4,000 molecules $^{125}$I-tPA bound per naive RBC, see column 3 of Table 2). These data demonstrated that immunotargeting of anti-CR1/tPA in vivo was likely specific and restricted predominantly to RBC.

To examine the fibrinolytic activity of the resultant human anti-CR1/tPA-RBC complex, radiolabeled fibrin clots were used as described before. Anti-CR1/tPA-RBC lysed fibrin and blood clots demonstrating that tPA coupled to RBC via the anti-CR1 antibody retains its functional activity. Lysis of clots by IgG/tPA-RBC used as controls was approximately ten times less effective (Table 3, column 5, bottom row) and did not differ significantly from the background level of fibrinolysis mediated by naive RBC.

TABLE 3

Coupling of Activators with RBCs in Whole Blood

| Activator | Added (per RBC) | Bound (per RBC) | % Bound (of added) | % Lysis (fibrin clot) | % Fibrinolysis (blood clot) |
|---|---|---|---|---|---|
| anti-CR1/$^{125}$I-suPAr | $10^4$ | 2,900 + 200 | 30% | ND | ND |
| IgG/$^{125}$I-suPAr | $10^4$ | 68 + 30 | 0.6% | ND | ND |
| anti-CR1/$^{125}$I-tPA | $5 \times 10^3$ | 2,600 + 150 | 55% | 28 + 4 | 87 + 6 |
| IgG/$^{125}$I-tPA | $5 \times 20^3$ | 50 + 45 | 0.9% | 3 + 1 | 18 + 3 |

Studies were then performed to examine the transfer of tPA from its carrier RBC to tissue, specifically vascular tissue. As a model for pulmonary vasculature transfer, human umbilical vein endothelial cells (HUVEC) cells were used in culture. RBC carriers were constructed by the method of the present invention. The RBCs carried either no protein (naive RBC), tPA (tPA/RBC, suPAr (suPAr/RBC), scuPA conjugated to suPAr molecules (scuPA-suPAr/RBC), scuPA (scuPA/RBC), or anti-TM/RBC. RBC carrying the protein molecules ($3 \times 10^4$ molecules/RBC) were incubated with HUVEC ($2 \times 10^7$ RBC per well, 160 minutes at 37° C.). Non-bound cells were eliminated by gentle washing with a phenol-free medium and 1 ml of water was added to lyse bound RBC. The number of HUVEC-bound RBC was determined by measuring the absorbance at 405 nm emitted by hemoglobin released into the cell lysates and expressed as 1,000 RBC/well. The results are shown in Table 4.

TABLE 4

Adhesiveness of complexes to endothelium in culture

| | Naive RBC | tPA/ RBC | suPAr/ RBC | scuPA-suPAr/ RBC | scuPA/ RBC | anti-TM/RBC |
|---|---|---|---|---|---|---|
| RBC bound | 2.6 | 1.7 | 2.5 | 2.3 | 22 | 11 |

Neither tPA/RBC, suPAr/RBC, nor scuPA-suPAr/RBC were adhesive to HUVEC, as evidenced by binding levels comparable to naive RBC. In contrast, scuPA/RBC complex or RBC conjugated with antibody against endothelial surface glycoprotein, thrombomodulin (used as a positive control) were highly adhesive. Accordingly, complexes comprising a soluble form of urokinase receptor biocompatibly coupled to a red blood cell carrier minimize the potential hazardous interactions of urokinase with endothelial cells.

Next, $^{125}$I-tPA/RBC were incubated with HUVEC, the unbound RBC removed by washing and $^{125}$I in the wells measured. HUVEC bound $8.1+0.2 \times 10^9$ molecules tPA/well after incubation with $^{125}$I-tPA/RBC. The results shown in Table 4 indicate that only 5% of this amount of cell-bound $^{125}$I-tPA was attributable to RBC-associated tPA in the wells ($3 \times 10^4$ molecules $^{125}$I-tPA/RBC×$1.7 \times 10^3$ RBC/well=$5.1 \times 10^8$ molecules RBC/$^{125}$-tPA/well). Therefore, tPA transfers from RBC to HUVEC, demonstrating the successful use of the RBC carrier of the instant invention. Accordingly, the present invention provides novel compositions for prolonging the half-life of drugs including fibrinolytics such as plasminogen activators and anticoagulants in the bloodstream of animals including humans by decreasing the degradation and elimination of the drugs in the bloodstream. The present invention also provides a method for increasing dissolution of fibrin clots by plasminogen activators in blood of a patient which comprises administering to a patient a composition comprising plasminogen activators biocompatibly coupled to red blood cell carriers. Thus, the compositions of the present invention are useful in preventing and treating uncontrolled formation of intravascular clots in a patient by administering to a patient suffering from uncontrolled formation of intravascular clots a composition comprising a fibrinolytic or anticoagulant drug biocompatibly coupled to red blood cell carriers.

Preparation of compositions comprising biocompatible red blood cell carriers is performed in accordance with known methods of conjugation and is exemplified by monovalent crosslinkage via biotin, streptavidin, and monoclonal antibodies. However, as will be obvious to those of skill in the art upon this disclosure, other methods of biocompatible coupling, i.e., chemical conjugation, noncovalent binding via a conjugated receptor, or other means of attachment which does not lead to poor biocompatibility of the RBC carrier exemplified by lysis and increased phagocytosis could also be used. In a preferred embodiment, the compositions of the present invention further comprise pharmaceutically acceptable vehicles for intravenous administration to patients with a disease or condition characterized by uncontrolled intravascular fibrin clot formation including deep venous thrombosis. In addition to plasminogen activators, it is believed that this delivery system will also be useful in delivering other drugs, such as anticoagulants. Compositions of the present invention are preferably administered systemically as a bolus intravenous injection of a single therapeutic dose of the drug (for example, 0.1–1.0 mg/kg for plasminogen activators).

The following nonlimiting examples are provided to further illustrate the present invention.

EXAMPLES

Example 1

Preparation of Conjugated Plasminogen Activators—Biotinylation, Radiolabeling of Proteins, Conjugation of Proteins to RBC and Assessment of the Fibrinolytic Activity Biotin ester, 6-biotinylaminocaproic acid N-hydroxysuccinimide ester (BxNHS) was dissolved in 100% dimethylformamide to a final concentration of 10 mM or 1 mM. Tissue-type plasminogen activator (tPA), urokinase, streptokinase and soluble urokinase plasminogen activator receptor (suPAr) were biotinylated at ten-fold molar excess of BxNHS. Eight microliters of fresh 1 mM BxNHS were added to 100 µl of a protein solution (1 mg/ml in borate buffered saline, BBS, pH 8.1). After a 1 hour incubation on ice, excess of non-reacted BxNHS was eliminated by overnight dialysis. Biotinylated proteins were radiolabeled with $^{125}$Iodide using Iodogen-coated tubes according to the manufacturer's recommendations (Pierce). Incubation of 100 µg of a biotinylated protein and 100 µCi of sodium $^{125}$Iodide in a tube coated with 100 µg of Iodogen for 20 minutes on ice yielded streptavidin with a specific radioactivity of approximately 500 cpm per ng. Excess iodine was eliminated by dialysis. More than 95% of radiolabeled proteins were precipitable by TCA.

Two milliliters of fresh heparinized blood was then centrifuged at 1,500 rpm for 5 minutes and supernatant (i.e., plasma) was eliminated. The pellet was then resuspended and washed with PBS by standard centrifugation (10 ml of PBS per 1 ml of pellet, 1,500 rpm, 5 minutes, four times) to make a 100% suspension of washed RBC. PBS (0.9 ml) was then added to 0.1 ml of RBC pellet (i.e., make 10% suspension of washed RBC). One hundred microliters of 300 mM boric acid (pH 9.0) was added to 1.0 ml of 10% RBC. BxNHS in DMFA was then added to this suspension to obtain a final BxNHS concentration in the reaction mixture equal to 10 µM and to obtain $b_{10}$-RBC. At first, 1 µl of stock solution of 0.1 M BxNHS/DMFA was added to 99 µl DMFA. Then 10 µl of this fresh 1 mM BxNHS/DMFA was added to 1 ml 10% RBC and mixed well. After a 30 minute incubation with periodic gentle shaking, at 20° C., excess non-reacted BxNHS was eliminated from the reaction mixture by standard centrifugation with PBS containing 2 mg/ml BSA (BSA-PBS). A 10% suspension of biotinylated RBC in BSA-PBS was prepared.

To attach streptavidin to b-RBC, 20 µl of SA stock solution (1 mg/ml in PBS) was added to 100 µl 10% suspension of b-RBC and mixed well. This provides addition of 1 µg SA per $5 \times 10^6$ b-RBC (about $2 \times 10^6$ molecules per b-RBC). After a 30 minute incubation with periodic gentle shaking at 20° C., non-bound SA was removed by standard centrifugation in BSA-PBS.

To attach biotinylated plasminogen activator or suPAr to SA/b-RBC, 5 µl of stock solution b-PA or b-suPAr (1 mg/ml in PBS) was added to 100 µl 10% suspension of SA/b-RBC and mixed well. This provides addition of 1 µg b-PA or b-suPAr per $2 \times 10^7$ SA/b-RBC (about $3.5 \times 10^5$ molecules per SA/b-RBC). b-PA or b-suPAr was then incubated with the 10% suspension of SA/b-RBC for 1 hour (periodic gentle shaking, 20° C.). Non-bound proteins were removed by standard centrifugation with BSA-PBS. To quantitate binding of b-PA or b-suPAr to SA/b-RBC, radiolabeled b-PA or b-suPAr was used as a tracer.

Example 2

In Vivo Administration of Conjugated Plasminogen Activators

To study biodistribution of radiolabeled preparations in rats, injection of 0.5 ml of saline containing 1 µg of radiolabeled PA or suPAr, or these proteins coupled to the carrier RBC, was made into the tail vein under anesthesia. To trace RBC-coupled plasminogen activators after in vivo administration, 20–50 µl of 10% suspension of $^{125}$I-b-PA/SA/b-RBC was injected via the tail vein in anesthetized rats. At indicated time after injection (5 minutes—24 hours), anesthetized rats were sacrificed by exsanguination. Blood and internal organs were collected. Organs were rinsed with saline until free of blood and weighed. Radioactivity of $^{125}$I in aliquots of blood and internal organs was then determined using a gamma-counter. Plasma was then separated from the blood by centrifugation of blood and radioactivity in the plasma was determined. Results were calculated as cpm per gram of tissue, blood or plasma, as mean±standard error (M±SE). Statistical comparisons were made using one-way analysis of equal variance (ANOVA) followed by Student-Newman-Keuls Method at a level of statistical significance of $p < 0.05$.

What is claimed is:

1. A composition comprising a plasminogen activator or a receptor for urokinase plasminogen activator conjugated by chemical crosslinking with a human CR1 monoclonal antibody specific for red blood cells so that said composition provides specific biocompatible coupling of the plasminogen activator to red blood cells thereby limiting non-specific binding and tissue uptake of the plasmi-nogen activator while maintaining antithrombotic activity of the plasminogen activator.

2. A composition comprising a plasminogen activator or a receptor for urokinase plasminogen activator conjugated with a human CR1 monoclonal antibody specific for red blood cells, wherein the plasminogen activator or receptor for urokinase plasminogen activator and the human CR1 monoclonal antibody specific for red blood cells are biotinylated and conjugation is via streptavidin, so that said composition promotes specific biocorapatible coupling of the plasminogen activator to red blood cells thereby limiting nonspecific binding and tissue uptake of the plasminogen activator while maintaining anti-thrombotic activity of the plasminogen activator.

3. A composition comprising a plasminogen activator conjugated with a human CR1 monoclonal antibody specific for red blood cells so that said composition provides specific biocompatible coupling of the plasminogen activator to red blood cells thereby limiting non-specific binding and tissue uptake of the plasminogen activator while maintaining antithrombotic activity of the plasminegen activator.

* * * * *